United States Patent
Palepu et al.

(10) Patent No.: US 9,655,898 B2
(45) Date of Patent: May 23, 2017

(54) PHARMACEUTICAL COMPOSITIONS CONTAINING PEMETREXED HAVING EXTENDED STORAGE STABILITY

(75) Inventors: Nagesh R. Palepu, Southampton, PA (US); Philip Christopher Buxton, Essex (GB)

(73) Assignee: EAGLE PHARMACEUTICALS, INC., Woodcliff Lake, NJ (US)

( * ) Notice: Subject to any disclaimer, the term of this patent is extended or adjusted under 35 U.S.C. 154(b) by 0 days.

(21) Appl. No.: 13/806,624

(22) PCT Filed: Jul. 26, 2011

(86) PCT No.: PCT/US2011/045341
§ 371 (c)(1),
(2), (4) Date: Feb. 6, 2013

(87) PCT Pub. No.: WO2012/015810
PCT Pub. Date: Feb. 2, 2012

(65) Prior Publication Data
US 2013/0231357 A1 Sep. 5, 2013

Related U.S. Application Data

(60) Provisional application No. 61/368,544, filed on Jul. 28, 2010.

(51) Int. Cl.
*A61K 31/519* (2006.01)
*A61K 9/08* (2006.01)
*A61K 47/10* (2006.01)
*A61K 47/12* (2006.01)
*A61K 47/18* (2006.01)

(52) U.S. Cl.
CPC .............. *A61K 31/519* (2013.01); *A61K 9/08* (2013.01); *A61K 47/10* (2013.01); *A61K 47/12* (2013.01); *A61K 47/183* (2013.01)

(58) Field of Classification Search
None
See application file for complete search history.

(56) References Cited

U.S. PATENT DOCUMENTS

| 4,931,441 A | * | 6/1990 | Lawrence | 514/249 |
| 6,686,365 B2 | * | 2/2004 | Riebesehl et al. | 514/262.1 |
| 2007/0099866 A1 | * | 5/2007 | Moser et al. | 514/49 |
| 2009/0324552 A1 | * | 12/2009 | Lichter et al. | 424/93.4 |

FOREIGN PATENT DOCUMENTS

| WO | WO 2010/030598 | * | 3/2010 | A61K 9/20 |

* cited by examiner

*Primary Examiner* — Bethany Barham
*Assistant Examiner* — Barbara Frazier
(74) *Attorney, Agent, or Firm* — Lucas & Mercanti, LLP

(57) ABSTRACT

Long term storage stable pemetrexed-containing liquid pharmaceutical compositions are disclosed. The compositions can include pemetrexed or pharmaceutically acceptable salts thereof; an antioxidant selected from lipoic acid, dihydrolipoic acid, methionine and mixtures thereof; a chelating agent selected from lactobionic acid, sodium citrate, tribasic and mixtures thereof; and a pharmaceutically acceptable fluid. The pH of the compositions is in a range of about 8 to about 9.5. The pemetrexed-containing compositions have less than about 5% total impurities, on a normalized peak area response ("PAR") basis as determined by high performance liquid chromatography ("HPLC") at a wavelength of 227 nm, after at least about 18 months of storage at a temperature of from about 5° C. to about 25° C. Methods of preparing the formulation as well as methods of treatment of pemetrexed-susceptible diseases using the same are also disclosed.

18 Claims, No Drawings

PHARMACEUTICAL COMPOSITIONS CONTAINING PEMETREXED HAVING EXTENDED STORAGE STABILITY

CROSS-REFERENCE TO RELATED APPLICATIONS

This patent application is a U.S. national phase under 35 U.S.C 371 of PCT/US2011/045341 filed on Jul. 26, 2011, which claims the benefit of priority under 35 U.S.C. §119(e) to U.S. Provisional Patent Application No. 61/368,544, filed on Jul. 28, 2010, entitled "PHARMACEUTICAL COMPOSITIONS CONTAINING PEMETREXED HAVING EXTENDED STORAGE STABILITY", the contents of each of which are incorporated herein by reference in their entirety.

BACKGROUND OF THE INVENTION

Pemetrexed disodium heptahydrate has the chemical name L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate. The structural formula is as follows:

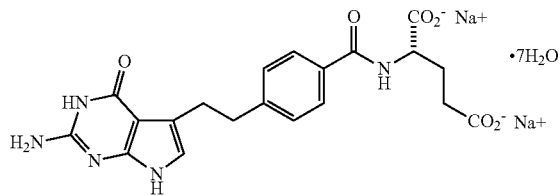

Pemetrexed is used in the treatment of malignant pleural mesothelioma and non-small cell lung cancer. The commercially-available product, ALIMTA, is supplied as a sterile lyophilized powder for intravenous infusion available in single-dose vials.

The relatively rapid formation of degradants is generally accepted as one of the factors which has prevented aqueous pemetrexed formulations having long-term stability from being commercially available. Five 5 major degradants of pemetrexed have been observed. Under acidic conditions, decarboxylation of glutamic acid is observed. Under alkaline conditions, degradation proceeds by side chain amide hydrolysis followed by deamination. In the presence of oxygen, two oxidative degradants result.

U.S. Pat. No. 6,686,365 discloses that ready to use (RTU) formulations of pemetrexed, which contain monothioglycerol, L-cysteine or thioglycolic acid. The '365 patent also disclosed that formulations which can be stored at room temperature are desirable. However, pemetrexed-containing formulations containing one of monothioglycerol, L-cysteine or thioglycolic acid referred to in the '365 patent when included at their recommended concentrations of 2.4 mg/ml, together with pemetrexed at a concentration of 25 mg/ml failed to demonstrate sufficient long term stability. The drug content fell well below acceptable levels.

There is a need to provide RTU liquid formulations of pemetrexed that have long term storage stability.

SUMMARY OF THE INVENTION

Liquid formulations in accordance with the present invention include pemetrexed (PMT) or a pharmaceutically acceptable salt thereof; an antioxidant such as lipoic acid, dihydrolipoic acid, methionine and mixtures thereof; a chelating agent such as lactobionic acid, sodium citrate, tribasic (tri sodium citrate dihydrate) and mixtures thereof; and optionally up to about 75% propylene glycol. The pH of the compositions is in a range of from about 8 to about 9.5. Further aspects of the invention include methods of treatment using pemetrexed-containing compositions and kits containing the same.

One of the advantages of the inventive formulations is that they have substantially improved long term stability when compared to currently available formulations. The inventive pemetrexed-containing formulations are substantially free of impurities after at least about 18 months at a temperature of from about 5° C. to about 25° C. The inventive formulations are advantageously ready to use or ready for further dilution.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT<1 elutes before the main peak, and any peak with an RRT>1 elutes after the main peak.

For purposes of the present invention, "substantially free of impurities" shall be understood to include pemetrexed-containing compositions in which the amount of total impurities is less than about 5% of the sum of peak areas of all degradants, as calculated on a normalized peak area response ("PAR") basis as determined by high performance liquid chromatograph ("HPLC") at a wavelength of 227 nm, after a period of about 18 months at a temperature of from about 5° C. to about 25° C. The amount of impurities is further calculated as being based upon the original amount of pemetrexed (or salt thereof) being present in the composition or formulation.

In some aspects of the present invention, the HPLC method includes the following:

| Method identity | Gradient method |
| --- | --- |
| Column | Zorbax SB C8 |
|  | 250 × 4.6 mm, 5 µm |
| Buffer | Prepare 10 mM $KH_2PO_4$ solution and adjust pH to 2.5 with ortho phosphoric acid |
| Mobile Phase | Mobile Phase-A = Buffer |
|  | Mobile phase-B = Acetonitrile |
| Flow rate | 1.0 ml/min |
| Column Temperature | 30° C. |
| Auto sampler Temperature | 4° C. |
| Wavelength | 227 nm |
| Injection volume | 20 µL |
| Diluent | Milli-Q water |
| Working concentration of Standard | 0.1 mg/ml |
| Working concentration of sample | 0.1 mg/ml |

-continued

| Method identity | Gradient method | |
|---|---|---|
| Retention time | Around 27 min | |
| Runtime | 44 min (including 8 min. delay time) | |
| Gradient elution | Time | B Conc. |
| | 0.01 | 5% |
| | 15.00 | 14% |
| | 30.00 | 18% |
| | 35.00 | 18% |
| | 36.00 | 5% |

Preferably, the amount of any individual degradant in the inventive compositions does not exceed 2% PAR as determined by HPLC at a wavelength of 227 nm after storage periods of at least about 18 months at a temperature of from about 5° C. to about 25° C. In some aspects, the amount of time the inventive compositions demonstrate long term storage stability is at least about 18 months and preferably at least about 2 years when stored under the conditions described herein.

For purposes of the present invention, "long term storage" shall be understood to include at least time periods which are in excess of those observed when currently available lyophilized pemetrexed formulations are reconstituted. In some preferred aspects of the invention, the time for which long term storage are contemplated include periods of at least about 18 months or longer.

The temperatures in which the liquid compositions are preferably kept are said to be either room temperature or less (i.e., about 25° C. or less). While not required, it is contemplated that storage can be further increased if carried out (optionally) under refrigerated conditions.

For purposes of the present invention, "refrigerated conditions" shall be understood as being temperature below room temperature and preferably temperatures of less than about 10° C., preferably from about >0° C. to about 10° C., more preferably from about 2 to about 10° C., yet more preferably about 3 to about 8° C., and still more preferably about 5° C. The term "refrigerated" conditions shall further be understood as including maintaining the composition at a substantially constant temperature and storage conditions within this range.

In some aspects of the invention where the pemetrexed compositions of the present invention are RTU and are stored at room temperature, they remain in the temperature range described herein for substantially the entire period between shortly (generally no more than a few hours) after manufacture and shortly (generally no more than a few hours) before dilution and administration to the patient in need thereof.

In accordance with an aspect of the invention, there are provided long term storage stable pemetrexed-containing liquid pharmaceutical compositions, including:
  a) pemetrexed or a pharmaceutically acceptable salt thereof;
  b) an antioxidant selected from lipoic acid, dihydrolipoic acid, methionine and mixtures thereof;
  c) a chelating agent selected from lactobionic acid, sodium citrate, tribasic and mixtures thereof; and
  d) a pharmaceutically acceptable fluid.

The total impurities in the inventive composition resulting from the degradation of the pemetrexed in the compositions is less than about 5% PAR as determined by HPLC at a wavelength of 227 nm, after at least about 18 months of storage at a temperature of from about 5° C. to about 25° C., and thus have long term stability for at least the same period of time or longer. Preferably, the pemetrexed-containing compositions demonstrate long term storage stability for at least about 2 years. In one embodiment, the amount of total impurities in the inventive compositions resulting from the degradation of the pemetrexed is less than about 3% PAR as determined by HPLC at a wavelength of 227 nm after at least about 2 years at a temperature of from about 5° C. to about 25° C. In another embodiment, the amount of total impurities is less than about 1% PAR as determined by HPLC at a wavelength of 227 nm, after at least about 18 months of storage at a temperature of from about 5° C. to about 25° C.

As used herein, the term "pemetrexed" refers to the stable salts, acids and free base forms thereof. The term includes, for example, the free acid, the pharmaceutically acceptable alkali metal, alkaline earth metal, non-toxic metal, ammonium, and substituted ammonium salts, such as for example, the sodium, potassium, lithium, calcium, magnesium, aluminum, zinc, ammonium, trimethylammonium, triethylammonium, mono ethanolammonium, triethanolammonium, pyridinium, substituted pyridinium, and the like. Any of the pemetrexed salts or related folic acid anti-metabolites known, including those described in U.S. Pat. No. 7,138,521, the contents of which are incorporated herein by reference, may be included in the formulations described herein. The disodium salt of pemetrexed is a preferred salt for the pharmaceutical compositions described herein.

In some aspects of the invention, the pemetrexed concentration is from about 1 mg/ml to about 100 mg/ml, preferably from about 10 mg/ml to about 50 mg/ml, and more preferably about 10 mg/ml to about 30 mg/ml. Preferably, the pemetrexed concentration in the inventive compositions is from about 20 mg/ml to about 25 mg/ml. It will be understood that compositions containing any useful concentration within the ranges, i.e. 1, 10, 15, 20, 25, 30, 35, 40, 50, 75, 100 are contemplated. In other embodiments, the pemetrexed concentration in the composition is about 25 mg/ml. In alternative aspects, the amount of pemetrexed is outside these ranges but the amounts will be sufficient for single or multiple administrations of dosages generally regarded as effective amounts.

For purposes of the present invention, a pharmaceutically acceptable fluid is a fluid which is suitable for pharmaceutical use such as aqueous solutions, water, saline, $D_5W$, etc., optionally containing preservatives, tonicity, osmolality, buffers, etc., well known to those of ordinary skill in the art. Preferably, the pharmaceutically acceptable fluid includes water.

In several embodiments of the invention, the pharmaceutical compositions include water as a pharmaceutically acceptable fluid. In other embodiments of the invention, however, the pharmaceutical compositions include a mixture of propylene glycol (PG) and water. For example, in one embodiment, the pharmaceutical compositions include about 10% propylene glycol and about 90% water. Alternatively, the pharmaceutical compositions can include about 25% propylene glycol and about 75% water. In other embodiments, the pharmaceutical compositions can include up to about 75% propylene glycol. The amount of water and propylene glycol can be varied within the ranges, i.e. the ratio of water to propylene glycol in the pharmaceutical compositions can range from about 100% to 0% to about 25% to up to about 75%. Within this range, are pemetrexed-containing pharmaceutical compositions including up to about 75% propylene glycol and greater than about 25% water, and pharmaceutical compositions including about 50% water and 50% propylene glycol.

The pemetrexed-containing compositions according to several preferred aspects of the invention include a solubilized amount of antioxidant. For purposes of the present invention, "solubilized amount" shall be understood to include the saturation solubility concentration, where adding more antioxidant does not increase the concentration of the antioxidant in the final formulation of the pemetrexed-containing compositions described herein. The amount of antioxidant included in the formulations described herein will vary somewhat, depending upon the particular antioxidant and pemetrexed salt (or free base) selected and other factors known to those of ordinary skill. Within this guideline, suitable antioxidant concentrations in the compositions will be from about 1 mg/ml to about 25 mg/ml, or the saturation solubility, whichever is higher in the final formulation. Concentrations of the antioxidant range from about 2 mg/ml to about 10 mg/ml are preferred, and concentrations of from about 2.5 mg/ml to about 5 mg/ml are more preferred.

In some aspects of the invention, the chelating agent concentration in the inventive compositions is from about 0.005M to about 0.5M. In other aspects, the concentration of the chelating agent is from about 0.01M to about 0.1M, or from about 0.05M to about 0.1M. Preferably, the concentration of the chelating agent is about 0.05M.

Suitable antioxidants and chelating agents for inclusion include those which are pharmaceutically acceptable for use in human and veterinary formulations, although not limited to those currently regarded as safe by any regulatory authority. Particularly preferred antioxidants included in the pemetrexed-containing pharmaceutical compositions described herein are lipoic acid and L-methionine. Preferred chelating agents include sodium citrate, tribasic (also referred to as tri sodium citrate dihydrate), lactobionic acid, disodium ethylenediaminetetraacetic acid (EDTA) and tetrasodium EDTA.

Without meaning to be bound by any theory or hypothesis, metal ion induced oxidation of pemetrexed is caused by metal ions leached from the surface of the glass containers or from the elastomeric composition of the stopper in which pemetrexed formulations were stored. The presence of a chelating agent stabilizes pemetrexed solution during long term storage.

In several embodiments of the invention the pH of the formulations is from about 8 to about 9.5, preferably from about 8 to about 9 and more preferably to from about 8.5 to about 9. Preferably, the pH is about 8.5.

In view of the foregoing, some preferred long term storage stable pemetrexed-containing compositions in accordance with the invention include:

I.
 a) pemetrexed;
 b) L-methionine;
 c) sodium citrate, tribasic; and
 d) a pharmaceutically acceptable fluid; wherein
the composition has a pH of about 8.5; or II.
 a) pemetrexed;
 b) L-methionine;
 c) sodium citrate, tribasic; and
 d) propylene glycol and water; wherein
the composition has a pH of about 8.5.

Each of these compositions have the same stability profiles described above, i.e. having less than about 5% total impurities PAR, as determined by HPLC at a wavelength of 227 nm, after at least about 18 months of storage at a temperature of from about 5° C. to about 25° C. Preferably, the compositions include about 10% propylene glycol and about 90% water, or about 25% propylene glycol and about 75% water.

In accordance with other aspects of the invention, there are provided long term storage stable pemetrexed-containing compositions, including:
 a) pemetrexed or a pharmaceutically acceptable salt thereof;
 b) an antioxidant selected from lipoic acid, dihydrolipoic acid, methionine and mixtures thereof;
 c) a pharmaceutically acceptable fluid;
 d) at least about 60% propylene glycol; and
 e) an optional chelating agent selected from lactobionic acid, sodium citrate, tribasic and mixtures thereof.

These compositions also have the low levels of impurities and long term storage stability mentioned herein. Preferably these compositions include at least about 75% propylene glycol.

A further aspect of the invention includes a kit and/or pharmaceutical container for holding the pemetrexed-containing compositions described herein. As will be appreciated by those of ordinary skill, the kit will contain at least one pharmaceutically acceptable vial or container containing one or more doses of the pemetrexed-containing formulations/compositions as well as other pharmaceutically necessary materials for storing and/or administering the drug, including instructions for storage and use, infusion bag or container with normal saline or $D_5W$, additional diluents, if desired, etc. The diluent may also optionally include any known fluids capable of being included in sterile parenteral formulations. Such aqueous-based suitable fluids can include, for example, saline or dextrose if desired as well any of the known ancillary preservatives or excipients commonly found as part of parenteral formulations. In accordance with current FDA requirements, vials containing the inventive formulations contain well below the acceptable limits for particulate matter. Thus, the vials contain:

Particles=10 μm: Not more than 6000 per container (average)

Particles=25 μm: Not more than 600 per container (average).

The compositions of the present invention can be packaged in any suitable sterile vial or container fit for the sterile storage of a pharmaceutical such as pemetrexed for extended periods of time. Suitable containers can be glass vials, i.e. Schott treated vials, molded glass vials, and CZ resin vials, polypropylene or polyethylene vials or other special purpose containers. Containers are of a size sufficient to hold one or more doses of pemetrexed.

Without meaning to be bound by any theory or hypothesis, the glass vials, such as Schott treated vials, molded glass vials and CZ resin vials, minimize delamination and pitting of the glass.

In yet another aspect of the invention there are provided methods of treating a pemetrexed sensitive disease in mammals. Pemetrexed sensitive diseases include, but are not limited to, cancers, such as malignant pleural mesothelioma and non-small cell lung cancer. The methods include administering an effective amount of a pemetrexed-containing composition as described herein to a mammal in need thereof. Since the active ingredient portion of the inventive compositions is an FDA-approved drug, those of ordinary skill will recognize that the doses of pemetrexed employed in this aspect of the invention will be the similar to those employed in any treatment regimens designed for the drug as marketed under the trade name ALIMTA. The patient package insert containing dosing information is incorporated herein by reference. The methods of treatment also include administering the inventive formulations for any purpose or physical condition for which pemetrexed has been indicated as being useful.

A still further aspect of the invention includes methods of preparing the PMT compositions described herein. The methods include dissolving pemetrexed or pharmaceutically acceptable salt thereof in a sufficient amount of a pharmaceutically acceptable fluid containing an antioxidant, a chelating agent, and optionally propylene glycol, and adjusting the pH to from about 8 to about 9.5.

In a further aspect of the invention, there is provided a method of preventing the formation of pemetrexed degradants in liquid pemetrexed-containing formulations during long term storage at room temperature. The method includes dissolving a sufficient amount of pemetrexed or a pharmaceutically-acceptable salt thereof in a pharmaceutically acceptable fluid containing an antioxidant, a chelating agent, and optionally propylene glycol, adjusting the pH to from about 8 to about 9.5.

Further optional steps in accordance therewith include transferring one or more pharmaceutically acceptable doses of the formulations into a suitable sealable containing and storing the resultant solution in a sealed container at temperature of=about 25° C. As a result of carrying out these steps, it is possible to control or substantially prevent the formation of impurities which otherwise occur with pemetrexed-containing formulations having less than about 5% total impurities PAR as determined by HPLC at a wavelength of 227 nm, after at least about 18 months of storage at a temperature of from about 5° C. to about 25° C.

EXAMPLES

The following examples serve to provide further appreciation of the invention but are not meant in any way to restrict the effective scope of the invention.

Example 1

Comparative

The aqueous formulations described in the aforementioned '365 patent were prepared and tested for long term storage stability. The product of Example 1 of the '365 patent was made and thereafter transferred into vials which were sparged with $N_2$ prior to being sealed. The sealed vials were then subjected to accelerated stability testing for a period of three months at 40° C. The results obtained are presented in Table 1.

TABLE 1

Stability of PMT (40 mg/ml) with Thioglycerol and Sparged With $N_2$

| Formulation | Temp ° C. | Time (Months) | % Initial | % Total Impurities |
| --- | --- | --- | --- | --- |
| PMT - 40 mg/ml | | Initial | 100.0 | 0.29 |
| Thioglycerol-2.5 mg/ml | 40° C. | 1 M | 99.7 | 0.58 |
| pH 8.5 | | 2 M | 99.7 | 0.76 |
| Solution sparged with $N_2$ | | 3 M | 80.2 | 17.1 |

Note:
Total % impurities include total contributions from peaks at various RRTs.

As can be seen from Table 1 above, the product had sufficient stability for up to 2 months but degraded significantly on third month of storage at 40° C. Also, samples stored at 25° C. showed precipitate at the end of six months of storage. Pemetrexed-containing compositions with such high levels of degradation and precipitation on long term storage are not suitable for long term storage.

Example 2

Pemetrexed-containing compositions were prepared by dissolving pemetrexed disodium salt to a concentration of 25 mg/ml in water. L-methionine was added to a concentration of 5 mg/ml and sodium citrate, tribasic, or lactobionic acid was added as indicated in Table 2 below. The pH was adjusted to 8.5 with 0.1N NaOH. The samples were maintained at 40° C. and 25° C. and analyzed for drug content and impurity profile as indicated in Table 2 below. The results obtained are presented in Table 2.

TABLE 2

Stability of Pemetrexed with Antioxidant and Chelating Agent

| Formulation | Temp. | Time Period (Months) | Content (mg/mL) | % of Initial | % Total Impurities | pH Sample |
| --- | --- | --- | --- | --- | --- | --- |
| PMT - 25 mg/mL | | Initial | 27.6 | 100 | 0.00 | 8.4 |
| L-Methionine - 5 mg/mL | 40° C. | 1 M | 27.4 | 99.3 | 0.11 | 8.39 |
| Sodium citrate tribasic - | | 2 M | 27.2 | 98.6 | 0.23 | 8.37 |
| 0.05M | | 3 M | 27.2 | 98.6 | 0.33 | 8.38 |
| WFI qs to 1 mL | 25° C. | 3 M | 27.5 | 99.6 | 0.10 | 8.37 |
| pH 8.5 with 0.1N NaOH | | | | | | |
| PMT - 25 mg/mL | | Initial | 25.4 | 100 | 0.00 | 8.46 |
| L-Methionine - 5 mg/mL | 40° C. | 1 M | 25.3 | 99.6 | 0.05 | 8.44 |
| Lactobionic acid - 0.05M | | 3 M | 25.3 | 99.6 | 0.32 | 8.50 |
| WFI qs to 1 mL | | | | | | |
| pH 8.5 with 1N NaOH | | | | | | |

Note:
Total area % of impurities include total contributions from peak areas at various RRTs.

As shown in Table 2, the pemetrexed formulations are very stable in solutions containing an antioxidant and a chelating agent. Table 2 shows that pemetrexed, when dissolved at a concentration of about 25 mg/ml, in water and an antioxidant, such as methionine, and a chelating agent, such as sodium citrate, tribasic, at a pH of about 8.5, had less than 1% total impurities after about 3 months of storage at 40° C. and 25° C.

Table 2 also shows that pemetrexed-containing formulations including a mixture of L-methionine and lactobionic acid have less than 0.05% total impurities after 1 month of storage at 40° C.

The data presented in Table 2 translates to pemetrexed-containing formulations including an antioxidant and a chelating agent having a shelf life of as long as about 2 years under ambient storage conditions and even longer if kept refrigerated.

Example 3

Pemetrexed-containing formulations were prepared by dissolving PMT disodium salt to a concentration of 25 mg/ml in PG and water in a ratio as indicated in Table 3 below. L-methionine was added to a concentration of 5 mg/ml and sodium citrate, tribasic was added to a concentration of 14.7 mg/ml. The pH of the formulation was adjusted to 8.5 with 0.1N NaOH. The materials were stirred, filtered through 0.2 micron filter paper and 1 ml aliquots of the resultant formulation were transferred into vials and sealed. The samples were maintained at 40° C. and 25° C. as indicated in Table 3 below and analyzed periodically for drug content and total impurities.

TABLE 3

Stability of Pemetrexed with PG, Water, Antioxidant and Chelating Agent

| Formulation | Temp. | Time Period (Months) | Content (mg/mL) | % of Initial | % Total Impurities | pH Sample |
|---|---|---|---|---|---|---|
| PMT - 25 mg/mL | | Initial | 27.7 | 100 | 0.00 | 8.45 |
| L-Methionine - 5 mg/mL | 40° C. | 1 M | 27.5 | 99.3 | 0.05 | 8.43 |
| Sodium citrate, tribasic - 0.05M | | 3 M | 27.3 | 98.6 | 0.38 | 8.42 |
| PG:WFI (10:90) qs to 1 mL | | | | | | |
| pH - 8.5 with 0.1N NaOH | | | | | | |
| PMT - 25 mg/mL | | Initial | 26.7 | 100 | 0.00 | 8.47 |
| L-Methionine - 5 mg/mL | 40° C. | 1 M | 26.5 | 99.3 | 0.06 | 8.45 |
| Sodium citrate, tribasic - 0.05M | | 3 M | 27.1 | 101.5 | 0.35 | 8.46 |
| PG:WFI (25:75) qs to 1 mL | 25° C. | 3 M | 27.2 | 101.9 | 0.19 | 8.45 |
| pH - 8.5 with 0.1N NaOH | | | | | | |

Note: Total % impurities include total contributions from peaks at various RRTs.

Table 3 shows that pemetrexed, when dissolved in propylene glycol, water, an antioxidant, such as L-methionine, and a chelating agent, such as sodium citrate, tribasic, had substantially no increase in total degradants after 3 months. The data presented in Table 3 translates to pemetrexed-containing compositions including propylene glycol, water, an antioxidant and a chelating agent having a shelf life as long as about 2 years under ambient storage conditions.

Example 4

Pemetrexed-containing formulations were prepared by dissolving PMT disodium salt to a concentration of 25 mg/ml in PG and water in a ratio as indicated in Table 4 below. An antioxidant, or chelating agent, or both, were added as indicated in Table 4 below. The materials were stirred, filtered through 0.2 micron filter paper and 1 ml aliquots of the resultant formulation were transferred into vials and sealed. One of the samples was sparged with $N_2$ during manufacture as indicated in Table 4. The samples were maintained at 40° C. and 25° C. as indicated in Table 4 and analyzed periodically for drug content and total impurities.

TABLE 4

Stability of Pemetrexed with PG:Water (75:25)

| Formulation | Temp | Time (Months) | Content mg/ml | % Initial | % Total Impurities |
|---|---|---|---|---|---|
| PMT - 25 mg/mL | | Initial | 24.5 | 100.0 | 0.35 |
| Lipoic acid - 5 mg/mL | 40° C. | 1 M | 24.1 | 98.4 | 0.83 |
| PG:Water (75:25) qs to 1 mL | | 2 M | 24.0 | 98.0 | 2.50 |
| PMT - 25 mg/mL | | Initial | 24.7 | 100.0 | 0.36 |
| Lipoic acid - 2.5 mg/mL | 40° C. | 0.5 M | 24.6 | 99.6 | 0.46 |
| PG:Water(75:25) qs to 1 mL | | 1 M | 24.7 | 100.0 | 0.58 |
| pH - 8.0 with 0.01N NaOH | | | | | |
| Solution sparged with $N_2$ | | | | | |
| PMT - 25 mg/mL | | Initial | 24.8 | 100 | 0.00 |
| Lipoic acid - 2.5 mg/mL | 40° C. | 1 M | 24.4 | 98.4 | 0.27 |

TABLE 4-continued

Stability of Pemetrexed with PG:Water (75:25)

| Formulation | Temp | Time (Months) | Content mg/ml | % Initial | % Total Impurities |
|---|---|---|---|---|---|
| PG:Water (75:25) qs to 1 mL | | 2 M | 24.2 | 97.6 | 1.07 |
| | | 3 M | 23.6 | 95.2 | 1.08 |
| pH - 8.0 with 0.01N NaOH | 25° C. | 3 M | 24.7 | 99.6 | 0.40 |
| | | 6 M | 24.8 | 100 | 0.59 |
| | | 9 M | 24.5 | 98.8 | 1.06 |
| PMT - 25 mg/mL | | Initial | 24.5 | 100 | 0.34 |

TABLE 4-continued

Stability of Pemetrexed with PG:Water (75:25)

| Formulation | Temp | Time (Months) | Content mg/ml | % Initial | % Total Impurities |
|---|---|---|---|---|---|
| L-Methionine - 5 mg/mL | 40° C. | 1 M | 24.0 | 98.0 | 1.01 |
| PG:Water (75:25) | | 2 M | 23.7 | 96.7 | 1.22 |
| qs to 1 mL | | 3 M | 23.9 | 97.6 | 1.67 |
| pH-7.74 | 25° C. | 3 M | 25.2 | 102.9 | 0.87 |
| | | 6 M | 24.3 | 99.2 | 1.21 |
| | | 9 M | 24.3 | 99.2 | 1.32 |
| PMT - 25 mg/mL | Initial | | 24.4 | 100 | 0.00 |
| L-Methionine - 5 mg/mL | 40° C. | 1 M | 23.0 | 94.3 | 0.55 |
| Lactobionic acid - | | 2 M | 23.0 | 94.3 | 0.65 |
| 2 mg/mL | | 3 M | 23.3 | 95.5 | 1.06 |
| PG:Water (75:25) | 25° C. | 3 M | 24.4 | 100 | 0.44 |
| qs to 1 mL | | 6 M | 24.2 | 99.2 | 0.79 |
| pH-7.34 | | 9 M | 24.2 | 99.2 | 1.03 |

\* Low level of particulates observed

Note:
Total % impurities include total contributions from peaks at various RRTs.

As can be seen in Table 4, pemetrexed, when dissolved in water and propylene glycol in a ratio of 75:25, along with an antioxidant and a chelating agent the samples exhibit less than 1% impurities after storage for 2 months at 40° C. This data translates to pemetrexed-containing compositions having shelf life for at least 18 months under ambient storage conditions.

Table 4 also shows that pemetrexed-containing liquid pharmaceutical compositions including an antioxidant, a pharmaceutically acceptable fluid, at least about 60% propylene glycol, and optionally a chelating agent exhibits long term storage stability of at least 18 months under ambient storage conditions.

Example 5

Comparative

Pemetrexed-containing formulations were prepared by dissolving PMT disodium salt to a concentration of 25 mg/ml in PG and water as indicated in Table 5 below. Lipoic acid was added to a concentration of 2.5 mg/ml. The pH of the formulation was adjusted to 8.0 with 0.01N NaOH. The materials were stirred, filtered through 0.2 micron filter paper and 1 ml aliquots of the resultant formulation were transferred into vials and sealed. The samples were maintained at 40° C. and 25° C. as indicated in Table 5 below and analyzed periodically for drug content and total impurities. The results obtained are presented in Table 5 below.

TABLE 5

Stability of Pemetrexed with PG:Water (50:50) and Antioxidant

| Formulation | Temp | Time (Months) | Content (mg/ml) | % Initial | % Total Impurities |
|---|---|---|---|---|---|
| PMT - 25 mg/mL | Initial | | 24.9 | 100.0 | 0.20 |
| Lipoic acid - | 40° C. | 1 M | 24.0 | 96.4 | 1.84 |
| 2.5 mg/mL | | 2 M | 23.2 | 93.2 | 5.15 |
| PG:Water (50:50) | | 3 M | 22.2 | 89.2 | 10.1 |
| qs to 1 mL | 25° C. | 3 M | 24.6 | 98.8 | 1.81 |
| pH adjusted to 8.0 | | | | | |
| with 0.01N NaOH | | | | | |

Note:
Total % impurities include total contributions from peaks at various RRTs.

Table 5 shows that pemetrexed, when dissolved at a concentration of about 25 mg/ml, in 50% PG and 50% water and an antioxidant, without a chelating agent, had greater than about 10% total impurities after about 3 months storage at 40° C.

Pemetrexed-containing formulations having such levels of total impurities as those reported in Table 5 would not be suitable for long term storage.

Example 6

Comparative

Non-aqueous pemetrexed-containing formulations were prepared by mixing PMT disodium salt to a concentration of 25 mg/ml with PG and an antioxidant or chelating agent as indicated in Table 6 below. The materials were stirred, filtered through 0.2 micron filter paper and 1 ml aliquots of the resultant formulation were transferred into vials and sealed. The samples were maintained at 40° C. and 25° C. as indicated in Table 6 below and analyzed periodically for drug content and total impurities. The results obtained are presented in Table 6 below.

TABLE 6

Stability of Pemetrexed with PG and Antioxidant or Chelating Agent

| Formulation | Temp. | Time (Months) | Content mg/ml | % Initial | % Total Impurities |
|---|---|---|---|---|---|
| PMT - 25 mg/mL | Initial | | 24.4 | 100 | 0.00 |
| Lipoic acid - | 40° C. | 1 M | 24.1 | 98.8 | 0.54 |
| 2.5 mg/mL | | 2 M | 21.4 | 87.7 | 0.85 |
| PG qs to 1 mL | | | 21.4 | 87.7 | 1.01 |
| | | 3 M | 21.6 | 88.5 | 1.20 |
| | 25° C. | 3 M | 22.4 | 91.8 | 0.45 |
| | | 6 M | 22.7 | 93.0 | 0.61 |
| | | 9 M | 22.4 | 91.8 | 0.99 |
| PMT - 25 mg/mL | Initial | | 24.8 | 100 | 0.64 |
| Lipoic acid - | 40° C. | 1 M | 24.7 | 99.6 | 0.94 |
| 5 mg/mL | | 2 M | 24.5 | 98.8 | 1.75 |
| PG qs to 1 mL | | 3 M | 24.1 | 97.2 | 1.93 |
| | 25° C. | 3 M | 24.7 | 99.6 | 0.75 |
| | | 6 M | 24.6 | 99.2 | 1.19 |
| | | 9 M | 23.8 | 91.5 | 1.12 |
| PMT - 25 mg/mL | Initial | | 28.3 | 100 | 0.14 |
| Lactobionic acid - | 40° C. | 1 M | 28.4 | 100.4 | 0.99 |
| 2.5 mg/mL | | 2 M | 27.9 | 98.6 | 1.39 |
| PG qs to 1 mL | | 3 M | 27.9 | 98.6 | 2.17 |
| | | 6 M | 27.9 | 98.6 | 3.07 |
| | 25° C. | 3 M | 28.4 | 100.4 | 1.01 |
| | | 6 M | 28.2 | 99.6 | 1.32 |
| PMT - 25 mg/mL | Initial | | 28.8 | 100 | 0.26 |
| Lactobionic acid - | 40° C. | 1 M | 28.4 | 98.6 | 1.19 |
| 5 mg/mL | | 2 M | 28.3 | 98.3 | 1.90 |
| PG qs to 1 mL | | 3 M | 28.0 | 97.2 | 2.35 |
| | | 6 M | 27.9 | 96.9 | 3.06 |
| | 25° C. | 3 M | 28.5 | 99.0 | 1.14 |
| | | 6 M | 28.7 | 99.7 | 1.47 |

Note:
Total % impurities include total contributions from peaks at various RRTs.

Table 6 shows that non-aqueous pemetrexed-containing compositions, with pemetrexed at a concentration of about 25 mg/ml, in PG and an antioxidant, such as lipoic acid, had greater than about 1% total impurities after about 3 months storage at 40° C. Additionally, non-aqueous pemetrexed-containing compositions, in which pemetrexed is at a concentration of about 25 mg/ml, in PG and a chelating agent, such as lactobionic acid, had greater than about 3% total impurities after about 6 months storage at 40° C.

Non-aqueous pemetrexed-containing formulations having such levels of total impurities as those reported in Table 6 would not be suitable for long term storage.

We claim:

1. A long term storage stable pemetrexed-containing aqueous liquid pharmaceutical composition, comprising:
   a) pemetrexed or a pharmaceutically acceptable salt thereof;
   b) 1 mg/ml to about 20 mg/ml L-methionine; and
   c) 0.005M to about 0.5M sodium citrate, tribasic; and
   d) an aqueous pharmaceutically acceptable fluid; and optionally
   e) propylene glycol;
   wherein the composition has a pH of from about 8.0 to about 9.5; and
   said pemetrexed-containing composition has less than about 5% total impurities, on a normalized peak area response ("PAR") basis as determined by high performance liquid chromatography ("HPLC") at a wavelength of 227 nm, after at least about 18 months of storage at a temperature of from about 5° C. to about 25° C.

2. The long term storage stable pemetrexed-containing aqueous pharmaceutical composition of claim 1, wherein the pemetrexed is the disodium salt thereof.

3. The long term storage stable pemetrexed-containing aqueous pharmaceutical composition of claim 1, wherein the concentration of the pemetrexed is from about 1 mg/ml to about 50 mg/ml.

4. The long term storage stable pemetrexed-containing aqueous pharmaceutical composition of claim 1, wherein the concentration of the pemetrexed is from about 20 mg/ml to about 30 mg/ml.

5. The long term storage stable pemetrexed-containing aqueous pharmaceutical composition of claim 1, wherein the concentration of the pemetrexed is about 25 mg/ml.

6. The long term storage stable pemetrexed-containing aqueous pharmaceutical composition of claim 1, wherein the composition contains up to about 50% propylene glycol, relative to the total amount of the composition.

7. The long term storage stable pemetrexed-containing aqueous pharmaceutical composition of claim 6, wherein the composition contains about 10% propylene glycol, relative to the total amount of the composition.

8. The long term storage stable pemetrexed-containing aqueous pharmaceutical composition of claim 6, wherein the composition contains about 25% propylene glycol, relative to the total amount of the composition.

9. The long term storage stable pemetrexed-containing aqueous pharmaceutical composition of claim 6, wherein the composition contains about 30% propylene glycol, relative to the total amount of the composition.

10. The long term storage stable pemetrexed-containing aqueous pharmaceutical composition of claim 1, wherein the concentration of the L-methionine is from about 2.5 mg/ml to about 10 mg/ml.

11. The long term storage stable pemetrexed-containing aqueous pharmaceutical composition of claim 10, wherein the concentration of the L-methionine is about 5 mg/ml.

12. The long term storage stable pemetrexed-containing aqueous pharmaceutical composition of claim 1, wherein the concentration of the sodium citrate, tribasic is about 0.05M.

13. The long term storage stable pemetrexed-containing aqueous pharmaceutical composition of claim 1, wherein said long term storage is at least about 2 years.

14. The long term storage stable pemetrexed-containing aqueous pharmaceutical composition of claim 1, said pemetrexed-containing composition having less than about 1% total impurities, on a normalized peak area response ("PAR") basis as determined by high performance liquid chromatography ("HPLC") at a wavelength of 227 nm, after at least about 18 months of storage at a temperature of from about 5° C. to about 25° C.

15. A long term storage stable pemetrexed-containing aqueous liquid pharmaceutical composition, comprising:
   a) pemetrexed or a pharmaceutically acceptable salt thereof;
   b) 1 mg/ml to about 20 mg/ml of an antioxidant selected from the group consisting of lipoic acid, dihydrolipoic acid, methionine and mixtures thereof;
   c) 0.005M to about 0.5M of a chelating agent selected from the group consisting of lactobionic acid, sodium citrate, tribasic and mixtures thereof; and
   d) an aqueous pharmaceutically acceptable fluid; and
   e) up to 50% propylene glycol, relative to the total amount of the composition;
   wherein the pH is in a range of about 8 to about 9.5, and said pemetrexed-containing composition has less than about 1% total impurities, on a normalized peak area response ("PAR") basis as determined by high performance liquid chromatography ("HPLC") at a wavelength of 227 nm, after at least about 2 months of storage at a temperature of about 40° C.

16. The long term storage stable pemetrexed-containing aqueous pharmaceutical composition of claim 15, wherein the propylene glycol is present in an amount of about 10%, relative to the total amount of the composition.

17. The long term storage stable pemetrexed-containing aqueous pharmaceutical composition of claim 15, wherein the propylene glycol is present in an amount of about 25%, relative to the total amount of the composition.

18. A method of treating of a pemetrexed sensitive disease in mammals, comprising administering an effective amount of a long term storage stable pemetrexed-containing aqueous pharmaceutical composition of claim 1 to a mammal in need thereof.

* * * * *